United States Patent [19]
Cole, Jr.

[11] Patent Number: 5,311,274
[45] Date of Patent: May 10, 1994

[54] FIBER OPTIC REFRACTOMETER

[76] Inventor: Charles F. Cole, Jr., 332 N. Ridge Rd., Little Rock, Ark. 72207

[21] Appl. No.: 881,059

[22] Filed: May 11, 1992

[51] Int. Cl.$^5$ .................. G01N 21/41; G01N 33/38
[52] U.S. Cl. ................................ 356/133; 356/70; 356/128
[58] Field of Search .................. 356/133, 70, 128

[56] References Cited

U.S. PATENT DOCUMENTS

| | | | |
|---|---|---|---|
| 3,370,502 | 2/1968 | Wilks | 356/133 |
| 3,513,319 | 5/1970 | Broerman | 250/576 |
| 3,520,619 | 7/1970 | Ward | 356/130 |
| 3,619,068 | 11/1971 | Broerman | 356/133 |
| 3,639,770 | 2/1972 | Zizelmann | 356/133 |
| 3,779,352 | 11/1973 | White | 192/53 F |
| 3,850,528 | 11/1974 | DeBellis | 356/133 |
| 3,870,807 | 3/1975 | Baltes | 554/142 |
| 3,917,410 | 11/1975 | Ulrich | 356/133 |
| 3,932,038 | 1/1976 | Schweizer et al. | 356/133 |
| 3,999,857 | 12/1976 | David et al. | 356/133 |
| 4,187,025 | 2/1980 | Harmer | 356/133 |
| 4,221,962 | 9/1980 | Black et al. | 356/133 |
| 4,240,747 | 12/1980 | Harmer | 356/133 |
| 4,256,403 | 3/1981 | Powell | 356/133 |
| 4,306,805 | 12/1981 | Arrington | 356/133 |
| 4,372,165 | 2/1983 | Pitt et al. | 356/133 |
| 4,427,293 | 1/1984 | Harmer | 356/133 |
| 4,433,913 | 2/1984 | Harmer | 356/133 |
| 4,438,749 | 3/1984 | Schwippert | 356/133 |
| 4,544,840 | 10/1985 | Keller | 356/133 |
| 4,564,292 | 1/1986 | Omet | 356/133 |
| 4,639,594 | 1/1987 | Schoch et al. | 356/133 |
| 4,641,965 | 2/1987 | Harmer | 356/133 |
| 4,659,218 | 4/1987 | de Lasa et al. | 356/133 |
| 4,668,870 | 5/1987 | Okura | 356/133 |
| 4,678,904 | 7/1987 | Saaski et al. | 250/227.27 |
| 4,711,126 | 12/1987 | Houpt et al. | 356/133 |
| 4,745,293 | 5/1988 | Christensen | 356/133 |
| 4,746,179 | 5/1988 | Dahne et al. | 356/133 |
| 4,770,129 | 9/1988 | Miyata et al. | 356/133 |
| 4,798,954 | 1/1989 | Stevenson | 356/133 |
| 4,806,013 | 2/1989 | Bodenheimer et al. | 356/133 |
| 4,824,244 | 4/1989 | Miyata et al. | 356/133 |
| 4,827,121 | 5/1989 | Vidrine, Jr. et al. | 356/133 |
| 4,834,533 | 5/1989 | Horike et al. | 356/133 |
| 4,839,515 | 6/1989 | Kershaw | 356/133 |
| 4,843,248 | 6/1989 | Miyata et al. | 356/133 |
| 4,904,080 | 2/1990 | Afromowitz | 356/133 |
| 4,907,878 | 3/1990 | Arditty et al. | 356/133 |
| 4,936,681 | 6/1990 | Ruhrmann | 356/133 |
| 4,950,074 | 8/1990 | Fabricius et al. | 356/133 |
| 4,988,863 | 1/1991 | Bobb et al. | 356/133 |
| 5,026,139 | 6/1991 | Klainer et al. | 356/133 |

OTHER PUBLICATIONS

Ady Arie, Reuven Karoubi, Yigal S. Gur, and Moshe Tur Applied Optics—vol. 25, No. 11—Jun. 1, 1986 "Measurement and analysis of light transmission through a modified cladding optical fiber with applications to sensors".

P. M. Kopera, J. Melinger, and V. J. Tekippe Proceedings of the SPIE—vol. 412, pp. 82–89—1983 "Modified cladding wavelength dependent fiber optic temperature sensor".

Ady Arie, Moshe Tur, and Samuel Goldsmith SPIE—vol. 718 Fiber Optic and Laser Sensors IV (1986)—pp. 160–167 "Measurement and analysis of a modified cladding optical fiber with various input illuminations".

(List continued on next page.)

Primary Examiner—James C. Housel
Assistant Examiner—L. M. Crawford
Attorney, Agent, or Firm—J. Kevin Parker

[57] ABSTRACT

A fiber optic refractometer is disclosed for use in on-line measurement of the refractive index of a process fluid. The refractometer does not require light to pass through the process fluid and is hence unaffected by the presence of light diffusing particulate matter in the process fluid. A particular application for which the refractometer is well-suited is the on-line measurement of the hydrogenation state of edible oils (which correlates with refractive index) during the partial hydrogenation process.

18 Claims, 5 Drawing Sheets

OTHER PUBLICATIONS

W. Golunski, R. Hypszer, and J. Plucinski SPIE—vol. 1085 Optical Fibers and Their Applications V (1989)—pp. 473–475 "Optical fibre refractometer for liquid refractive index measurement".

D. J. David, D. Shaw, and H. Tucker Rev. Sci. Instrum., vol. 47, No. 9, Sep. 1976—pp. 989–997 "Design, development, and performance of a fiber optics refractometer: Application to HPLC".

A. L. Harmer Optical Fiber Sensors, 1983—pp. 104–108 "Optical fibre refractometer using attenuation of cladding modes".

Michael D. DeGrandpre and Lloyd W. Burgess Center for Process Analytical Chemistry, Dept. of Chemistry BG-10—pp. 821–830 "Evanescent field fiber optic probe for process analysis".

M. Gottlieb and G. B. Brandt Applied Optics—Nov. 15, 1981—vol. 20, No. 22—p. 3867 "Temperature sensing in optical fibers using cladding and jacket loss effects".

N. S. Kapany and J. N. Pike—Journal of the Optical Society of America vol. 47, No. 12—Dec., 1957—pp. 1109–1117 "Fiber Optics, Part IV. A Photorefractometer".

C. F. Cole, Jr., *Development of a Fiber Optic Refractometer to Measure the Partial Hydrogenation of Edible Oils.*, dissertation, Univ. of Arkansas, Fayetteville, Aug., 1991.

FIBER OPTIC REFRACTOMETER

BACKGROUND

Edible oils are those extracted from plant seeds, such as soybean, cottonseed, peanut, sunflower, corn, etc., and processed for human consumption. They are usually found as ingredients in foodstuffs such as bread, pastries, margarines, salad dressings and candies. Today, they are consistently used as the medium to fry foods. In practically all cases, these oils undergo the process of partial catalytic hydrogenation to prepare them for use in their intended product. Hydrogenation alters the molecular structure within the fatty ester chains of the oil triglyceride molecule by reducing the number of double carbon bonds that naturally occur.

Partial hydrogenation affects edible oils in two ways. First, it stabilizes the oil; it extends the time that the oil's flavor and smell are acceptable as a human food. Second, it converts the naturally occurring oils into forms that have melting and handling characteristics demanded by the application; the more an edible oil is hydrogenated, the higher its melting point becomes. For example, oils used in salad dressings must not coagulate on cold lettuce; margarine should remain firm on the breakfast table, yet melt on pancakes and biscuits; shortening should remain firm in the pie crust or cake batter, but quickly melt in the oven.

The basic batch hydrogenation process in use today has changed little since it was invented nearly a century ago. A closed vessel (converter) is filled with approximately 58,000 pounds of oil. The oil is heated to approximately 175° C. with steam passing through internal coils. Then roughly 10.5 pounds of nickel powder is added as a catalyst; hydrogen gas is introduced continuously into the bottom of the converter and the hydrogen is vigorously mixed into the oil and nickel powder by an agitator. The ensuing hydrogenation reaction is exothermic and is controlled by cooling water passing through the original steam coils. The converter operates at a pressure of 20 to 30 psi while still releasing excess hydrogen and processing effluents from the top of the converter. Hydrogenation is arrested immediately upon cessation of agitation which is normally done several times during the process. Processing times vary from 15 to 60 minutes depending on the desired degree of hydrogenation.

Although it is not a part of the actual hydrogenation process, about 30 pounds of diatomaceous earth are also added into the converter vessel along with the nickel catalyst. The diatomaceous earth is used as a filtering aid to remove the nickel from the oil at the termination of the process. The finished batch of oil is placed in a holding tank and continuously circulated through wire filter screens to cleanse the oil of the nickel catalyst. The diatomaceous earth is trapped on the wire screen filters, in effect becoming the filter itself. The nickel powder is in turn filtered out of the oil by this diatomaceous earth "cake." The "cake" is reclaimed off of the filter screens and the nickel recycled. All in all during the actual hydrogenation process, there is a 0.072% mixture (by weight) of nickel catalyst and diatomaceous earth present in the oil.

There are several ways of accurately determining the amount of hydrogenation of edible oils. One is the Wijs method, recommended by the American Oil Chemists, Society (AOCS). A large, measured amount of iodine monochloride reagent is added to a specific quantity of partially hydrogenated oil. The reagent "saturates" the oil by eliminating any double carbon bonds remaining in the various esters. The excess reagent is titrated with sodium thiosulfate, using starch as an indicator. The amount of iodine reagent lost is called the iodine value, a number that decreases with increased hydrogenation. This method, though accurate, is a laboratory procedure requiring 30 to 45 minutes to perform.

Another technique of determining the degree of partial hydrogenation is to measure the oil's refractive index (RI). There is a direct, linear relation between RI and iodine value. RI linearly decreases with increased hydrogenation. An example is the relationship between RI and iodine value (I) of cottonseed, peanut, soybean, and linseed oils. It has the form $$n_D^{40} = 1.4515 + (0.000117)I \qquad (1)$$

where $n_D^{40}$ is the RI at a wavelength of 589.3 nm and at 40° C. (See Bailey, A. E., Bailey's Industrial Oil and Fat Products, John Wiley & Sons, Inc., Vol. 2, 1982, pp. 40, 220). The AOCS Method Cc 7-25, "Refractive Index," is an accepted industry standard in determining the degree of edible oil hydrogenation. The technique is quick and can be performed in the process control room.

Several established designs of process refractometers are in common use today which depend upon light transmission through the oil in order to measure its RI. With any of these units, a reading can be made in a matter of minutes and a correlation of RI to iodine value read from a chart. The handicap with this method is that these refractometers operate on light transmission through the oil sample, and with nickel catalyst and diatomaceous earth in the oil, the transmitted light is diffused, making the refractometer response difficult to interpret. Therefore, an oil sample withdrawn from a batch of oil being processed must first be manually filtered before analysis. While the sample is being withdrawn, filtered and analyzed, the hydrogenation process must come to a standstill which sometimes means a delay of 10 to 20 minutes. It is common to have two or three test samples taken during the processing of an oil batch. Not only is this a worrisome delay to the oil processor, but also the accuracy and repeatability of the refractometer reading is subject to operator skill. It would be desirable to have an on-line refractometer that will perform accurately in the presence of catalyst and diatomaceous earth.

One type of refractometer that does not require light transmission through the process liquid, and hence is unaffected by the presence of catalyst and diatomaceous earth, is a critical angle refractometer. (See Maley, L. E., "Refractometers," Journal of Chemical Education, vol. 45, no. 6, 1968, pp. A467-A485.) Such a device consists of a glass prism or plate with a flat side mounted over a small opening in a pipe or tank wall. The back side of the glass (RI=$n_g$) is in direct contact with the process liquid (RI=$n_l$). Using Snell's law, a critical angle, $\theta_c$, for light incident at the glass-liquid interface is selected according to $$\theta_c = \arcsin \frac{n_l}{n_g} \qquad (2)$$

such that light is reflected back to a sensor when $$n_l \leq n_g \sin \theta_c \quad (3)$$

While the operation of this device is not affected by the turbidity of the process liquid, the device is only a fixed comparator and is thus unsuitable for continuous measurement of refractive index values. Also, $n_g$ must be greater than $n_l$ for there to be a critical angle.

Another type of refractometer which does not require light to pass through the process liquid, but offers a means of continuously measuring RI values, is a fiber optic refractometer. The efficiency with which optical fibers transmit light is determined by the disparity of RI that exists between the core and cladding materials. It follows that such a device could be used as a refractometer if the process liquid of interest became the "cladding" about a glass core. By measuring the efficiency at which such a fiber transmitted light energy, the RI of the liquid cladding could be determined. The concept of attenuated total reflectance (ATR) forms this major category of fiber optic refractometers. (See Kapany, N. S., and J. N. Pike, "Fiber Optics, part IV, a photorefractometer," Journal of the Optical Society of America, vol. 47, no. 12, 1957, pp. 1109-1117.) In these instruments, a conical beam of light with a uniform intensity, I watts/steradian, excites a glass rod or fiber (RI=$n_g$). The transmitted light is then measured by a photosensitive device. The following equations define the numerical aperture NA, and transmitted light power, Pt $$
\begin{aligned}
NA &= \sqrt{n_g^2 - n_l^2} \quad &(a) \\
Pt &= \pi I (NA)^2 = \pi I(n_g^2 - n_l^2) \quad &(b)
\end{aligned}
\quad (4)
$$

By measuring Pt, continuous values of $n_l$ may be calculated provided $n_g$ and I are known.

In order for the device to work, $n_l$ must be less than $n_g$. To overcome the problem of the refractometer losing all resolution when $n_l \geq n_g$, glass rods or fibers of a higher RI must be substituted.

A variation of the ATR fiber optic refractometer uses a laser beam incident on the end of the glass rod. (See David, et al., "Design, development and performance of a fiber optics refractometer: Application to HPLC," Review of Scientific Instruments, vol. 47, no. 9, 1976, pp. 989-997; also, U.S. Pat. No. 3,999,857, J. D. David, D. A. Shaw & H. C. Tucker, "Refractive Index Detector," 1976.) The beam angle into the rod is adjusted via a mirror moved by a micrometer until the edge of the "cone of acceptance" (i.e., the numerical aperture or NA) is found. Multiple reflections of the light propagating down the fiber make the transition very sharp. The micrometer reading correlates to the NA, and $n_l$ can be calculated from equation (4a). The instrument locates the sharp light transition at the edge of the NA, but its output drops to a low, constant level once the incident beam angle exceeds the NA.

A fiber optic refractometer using Fresnel's equations has also been designed. (See Meyer, M. S., and G. L. Eesley, "Optical Fiber Refractometer," Review of Scientific Instruments, vol. 58, no. 11, 1987, pp. 2047-2048.) Monochromatic light is transmitted down a single mode fiber and reflects off the far end of the fiber, immersed in the process liquid. The core (RI=$n_{co}$) at that end of the fiber is polished smooth, perpendicular to the fiber axis. Fresnel reflections from the core/liquid dielectric interface are transmitted back through the fiber to a photosensor. For light perpendicularly incident to such an interface, the Fresnel's reflection is $$R = \frac{(n_{co} - n_l)^2}{(n_{co} + n_l)^2} \quad (5)$$

The reflected light is correlated to equation (5), and the refractometer operates for values of $n_l$ either greater than or less than $n_{co}$. There is a reflection null at $n_{co}=n_l$. However, due to the quadratic dependence of the reflectance, it is impossible to tell which side of the reflection null the refractometer is operating on. The solution is to use two fibers of different RI and observe their relative outputs.

Fiber optic refractometers using bent fibers have also been developed. (See Golunski, W., et al., "Optical fiber refractometer for liquid refractive index measurement," Proceedings of the SPIE—Optical Fibers and Their Applications V, vol. 1085, 1990, pp. 473-475.) Bending the fiber effectively decreases $n_{co}$, reducing the NA of equation (4a). Consequently, the fiber's transmitted power, Pt of equation (4b) is also reduced. One paper, using a stripped, step index quartz fiber, describes how the range of such a refractometer's operation (analog range of Pt) can be varied by controlling the radius of the fiber bend; the smaller the radius, the lower the RI sensing range becomes. (See Harmer, et al., "Optical fibre refractometer using attenuation of cladding modes," Proceedings of First International Conference on Optical Fibre Sensors, Electronics Div., Institute of Electrical Engineers, 1983, pp. 104-108.) Such a refractometer is only functional when the liquid RI is less than the effective $n_{co}$.

Previous fiber optic refractometers, as described above, suffer from several shortcomings. First, analog optical responses are subject to variations in light source intensity and uniformity as well as light sensor sensitivity, liquid turbidity, operating temperatures and the bending of the optical fiber. Second, most responses of Pt versus liquid RI are nonlinear and must be compared to a complicated algorithm in order to maintain high accuracy. Third, there is no compensation for RI dispersion due to the light source wavelength. Fourth, mechanical measurement devices are affected by misalignment.

SUMMARY OF THE INVENTION

It is a primary objective of the present invention to provide a fiber optic refractometer which overcomes the problem described above and is thus particularly suitable for accurately determining the degree of partial hydrogenation of edible oils.

The present invention is a method and apparatus for measuring the refractive index (RI) of a process fluid. The invention is particularly suitable for the on-line measurement of the hydrogenation state of edible oils that still contain catalytic powder and other materials used in the hydrogenation process. In accordance with the invention, a section of optical fiber having no cladding is immersed in a cell containing the process fluid, the temperature of which is regulated and monitored. The RI of the fiber's core is known as a function of temperature and wavelength. Monochromatic light at a specified reference wavelength, $\lambda_R$, is radiated into one end of the fiber while the optical power transmitted through the fiber is measured at the other end. The temperature of the cell is then varied which causes the RIs of the process fluid and immersed optical fiber core to change in accordance with their respective dependencies on temperature. The varying of the cell temperature is continued until the optical power transmitted through the fiber reaches a minimum at which point the RIs of the fiber core and process fluid are deemed to be equal. The temperature, $T_{min}$, at which the transmission minimum occurs is noted. From the known functional relationship between the fiber core's RI with temperature and wavelength, the RI of the process fluid at $T_{min}$ and $\lambda_R$ can then be determined.

If the process fluid is known to belong to a class of fluids having as members liquids with different RIs but the same or similar dependencies of RI on temperature, measurement of the fluid's RI at $T_{min}$ allows the liquid to be identified within the class. Furthermore, from the known functional relationship between the fluid's RI and temperature, the RI of the fluid at any temperature can be calculated. Also, from the known functional relationship between the fluid's RI and light wavelength, the RI of the fluid at any light wavelength can be calculated. These aspects of the invention have particular applicability in determining the hydrogenation state (i.e., the extent of partial hydrogenation) of an edible oil but could be extended to other applications as well. In the former case, the known class of fluids would be a particular kind of edible oil such as either soybean, corn, or canola, etc. The members of the class are then those oils of that class having different hydrogenation states. Since the relationship of RI to temperature and wavelength can be determined for each particular edible oil (i.e., each class), the hydrogenation state of each oil can be determined from its RI as measured at $T_{min}$ and $\lambda_R$ and then corrected to any other temperature and wavelength.

It is contemplated that in the usual embodiment of the present invention, the optical fiber is a conventional step index design comprising a core surrounded by a cladding, a section of which has been removed, and is of circular cross-section. In other embodiments, however, the optical fiber could be any optical waveguide that gives a minimum power transmission at $T_{min}$. It may consist of a slab-like, rectangular core with one or more sides exposed to the process fluid.

Other objects, features, and advantages of the invention will become evident in light of the following detailed description considered in conjunction with the referenced drawings of a preferred exemplary embodiment according to the present invention.

DETAILED DESCRIPTION OF THE INVENTION

I. Theory

A typical optical fiber is a flexible dielectric structure designed to carry ultra-violet, visible or infrared light. It is composed of a core which is the "conduit" for the energy passing through the fiber, the cladding that surrounds the core and is in intimate contact with it, and the jacket that acts as a protective outer sheath and lends mechanical strength to the assembly. The core and cladding are both transparent to the light. They have RIs of $n_{co}$ and $n_{cl}$, respectively, with $n_{cl} < n_{co}$ such that optical radiation propagating along the core at angles greater than $\theta_c$ suffers total internal reflection at the core/cladding interface. Because the core and cladding are of uniform though differing RI, this type of fiber is called a step index design.

The numerical aperture (NA) of a step index optical fiber is derived by applying Snell's law to $\theta_c$, as viewed from the outside the fiber core end. The $\phi a$ is the vertex formed by the centerline of the optical fiber and an incident light ray.

$$NA = \sin\alpha \frac{1}{n_{ext}} \sqrt{n_{co}^2 - n_{cl}^2} \tag{6}$$

The NA assumes the fiber end is perpendicular to its axis and the external dielectric medium has a RI, $n_{ext}$. Usually, the external medium is air ($n_{ext} = 1$). Light rays entering the core at angles less than $\angle\alpha$ will be totally reflected as they propagate down the core. Rays falling outside $\angle\alpha$ will be transmitted into the cladding, according to Snell's law.

For these latter light rays there is partial reflectance, $R < 1$, each time they encounter the core/cladding interface, due to Fresnel's equations. After m reflections, these rays will be attenuated by $R^m$. Excellent rejection of non-totally reflected radiation occurs after 10 or more reflections which makes the fiber's transmission highly sensitive to the NA. Essentially all incident light outside the NA of an optical fiber is effectively rejected over a distance approximately equal to 50 times the core diameter.

Optical fibers can be categorized as multimode or single-mode according to their V number or normalized frequency defined by $$V = \frac{2\pi\rho}{\lambda} NA = \frac{2\pi\rho}{\lambda} \sqrt{n_{co}^2 - n_{cl}^2} \tag{7}$$

where $\rho$ is the core radius. For a multimode fibers $V > 1$, which implies that $\rho > \lambda$ and $NA > 0.1$. A large V number assures that geometric optics can be used to model the fiber, and that the NA of the fiber will propagate rays entering over a wide range of angles.

For a uniform point source of radiation of intensity I watts/steradian located in air at a distance, $D \leq \rho/NA$, from the optical fiber end, the amount of radiation falling within its NA is approximately $$Pt = \pi I(n_{co}^2 - n_{cl}^2) \tag{8}$$

For I and $n_{co}$ constant, the radiation power, Pt, transmitted through the optical fiber decreases as a function of $n_{cl}^2$. Equation (8) shows that Pt falls to zero when $n_{cl} = n_{co}$. At this coincidence, there exists no "core" and "cladding." There is just a single, homogeneous, dielectric medium. Non-coaxial radiation is never reflected, and it is lost.

Equation (8) indicates that when $n_{co}$ is a constant and $n_{cl} \leq n_{co}$ the transmitted power is a function of the cladding's RI. As discussed above, several papers have illustrated the principle that a step index optical fiber can be used to develop a refractometer. By stripping off the fiber's jacket and cladding over a short distance and immersing the exposed core in a liquid whose RI is less than the core RI, the transmitted power becomes a means of determining liquid (cladding) RI, provided that I and $n_{co}$ are known. Accurate measurement of such transmitted power, however, is difficult.

An optical fiber will still transmit power when $n_{cl} > n_{co}$. Fresnel's reflection equations show that reflection still occurs at any dielectric interface that may transmit light. Since any incident electromagnetic radiation energy, E, can be reduced to two orthogonal components, Fresnel's reflection equations are expressed in terms of two amplitude reflection coefficients $-r_\perp$ for the E component perpendicular to the incident plane and $r_\parallel$ for the E component parallel to the incident plane. The incident plane is defined by the incident ray and the normal to the dielectric interface at the point where the ray and interface intersect. The incident energy ray, $E_i$, as well as the reflected and transmitted energy rays, $E_r$ and $E_t$, all lie in the incident plane. Fresnel's equations, expressed in terms of light incident angle, $\theta_i$; incident dielectric RI, $n_i$; light transmitted angle, $\theta_t$; and transmission dielectric RI, $n_t$, are given in equations (9) and (10).

$$\left(\frac{E_r}{E_i}\right) \approx r = \frac{n_t \cos\theta_i - n_i \cos\theta_t}{n_t \cos\theta_i + n_i \cos\theta_t} \quad (9)$$

$$\left(\frac{E_r}{E_i}\right) \approx r = \frac{n_i \cos\theta_i - n_t \cos\theta_t}{n_i \cos\theta_i + n_t \cos\theta_t} \quad (10)$$

The reflection coefficients are related to the reflectances, $R_\perp$ and $R_\parallel$, which apply to measurements made by sensors sensitive to power $\propto |E|^2$.

$$R_\perp = r_\perp^2; \quad R_\parallel = r_\parallel^2 \quad (11)$$

Figure 1:
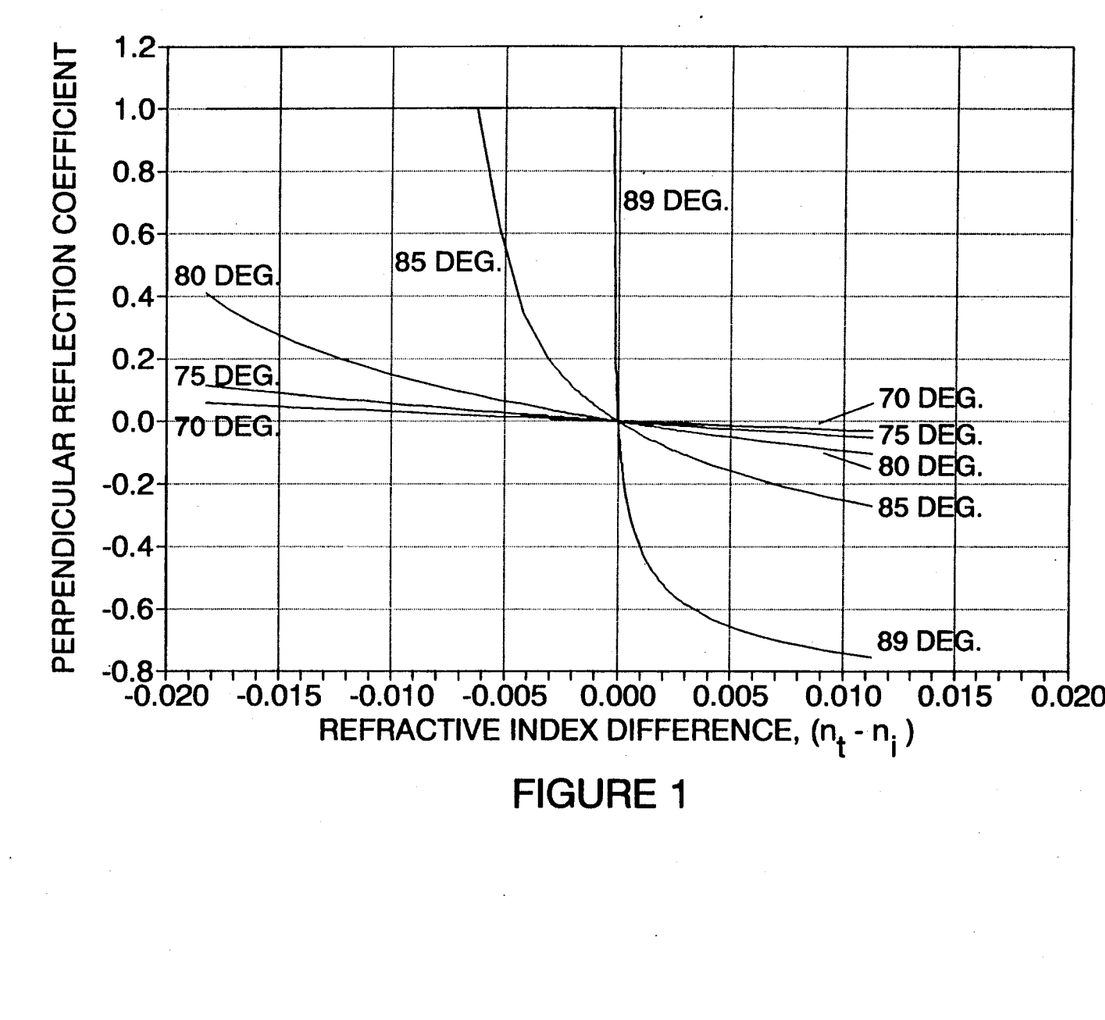
FIG. 1 is a graph of Fresnel's reflection coefficient, $r_{195}$, plotted against the refractive index difference $\Delta n = (n_t - n_i)$ for various incident angles $\theta_i$.
Figure 2:
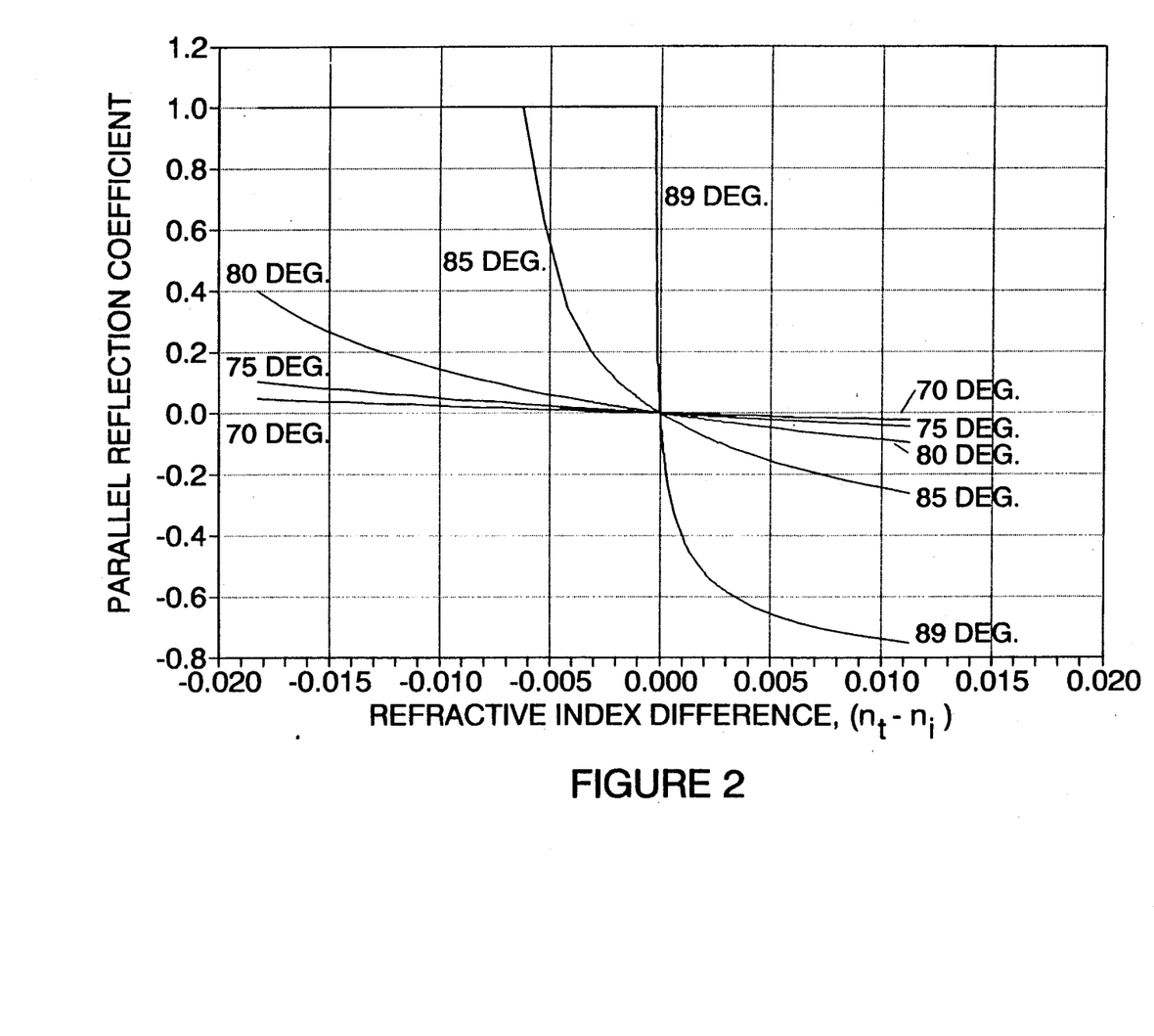
FIG. 2 is a graph of Fresnel's reflection coefficient, $r_{81}$, plotted against the refractive index difference $\Delta n = (n_t - n_i)$ for various incident angles $\theta_i$.
Figure 3:
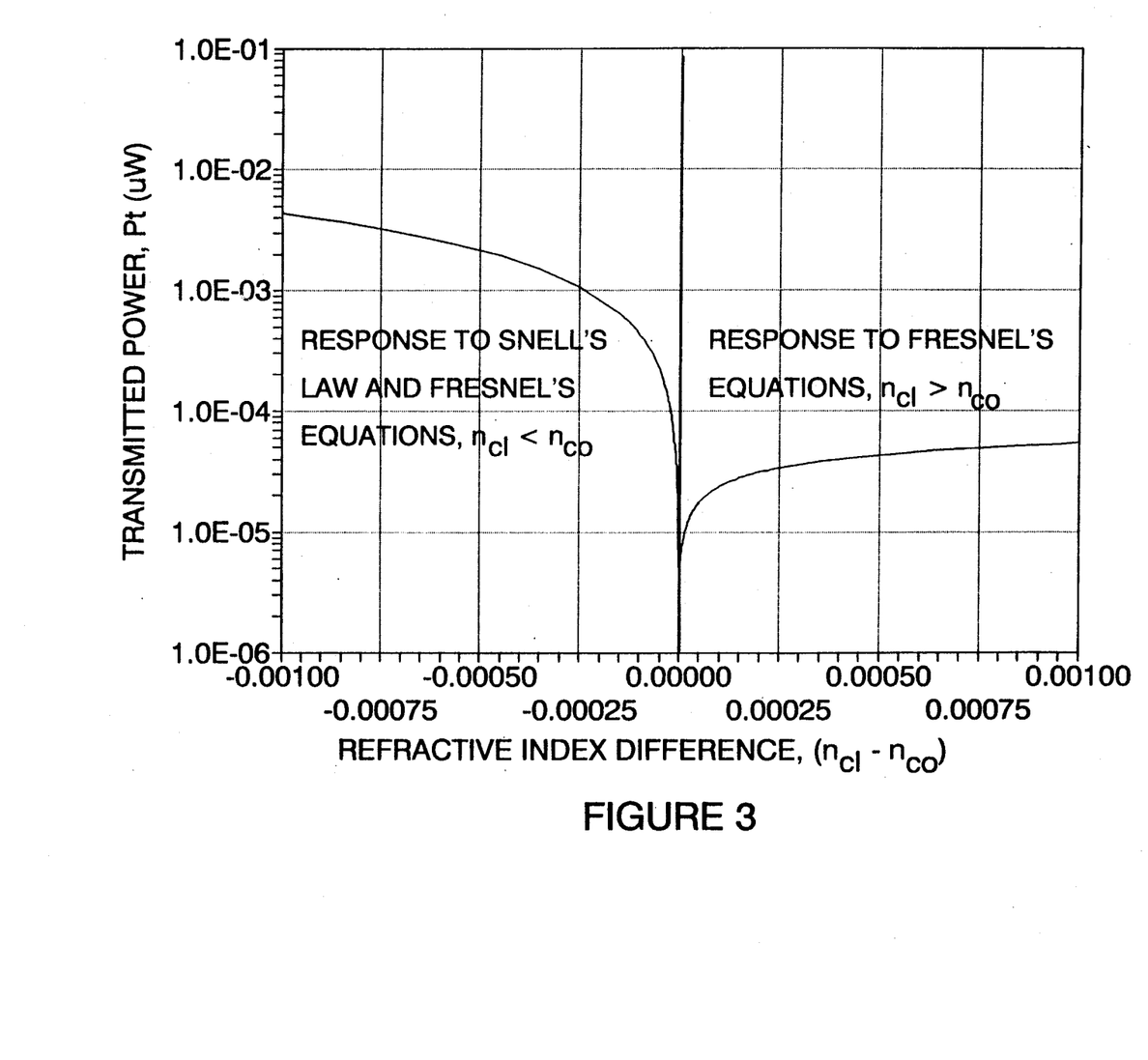
FIG. 3 is a graph of the transmitted light power response of a step index optical fiber with a section of core exposed to an "adjustable" cladding plotted against the refractive index difference.

FIGS. 1 and 2 demonstrate the sensitivity of $r_\perp$ and $r_\parallel$ as functions of $\Delta n = (n_t - n_i)$ and $\theta_i$. They show that for light striking a dielectric interface at large incident angles (i.e., nearly parallel to the dielectric interface), the reflection coefficients are significantly large even for very slight differences between $n_i$ and $n_t$. FIG. 3 combines the effects of Snell's law and Fresnel's equations on power transmitted through an optical fiber as a function of $(n_{cl} - n_{co})$. FIG. 3 assumes monochromatic light from a uniform point source, propagating through a multimode step index optical fiber having a section of modifiable cladding. FIG. 3 demonstrates a sharply defined power transmission minimum, $Pt_{min}$, as $n_{cl}$ approaches $n_{co}$. This sharp response forms the crux of the present invention to measure the RIs of edible oils, on-line and in real time, as they undergo partial hydrogenation.

The present invention, in contrast with previous devices, does not attempt to accurately measure transmitted light intensity in order to determine liquid RI. Rather, the approach is to vary (and measure) a parameter upon which the RIs of the cladding and core both depend until $n_{co} = N_{cl}$. A minimum of the transmitted light power intensity then occurs which is an easily measured endpoint.

Considering that the RIs of the core and "cladding" are functions of temperature and wavelength, and assuming that $Pt_{min}$ does occur, then the endpoint of interest is defined by $$n_{co}(T_{min}, \lambda_R) = n_{cl}(T_{min}, \lambda_R) \quad (12)$$

where $T_{min}$ and $\lambda_R$ are the temperature and wavelength existing at $Pt_{min}$. The RI of the "cladding" at some other temperature, $T_2$, and wavelength $\lambda_2$, may be expressed as shown in equation (13).

$$n_{cl}(T_2, \lambda_2) = n_{cl}(T_{min}, \lambda_R) + \int_{T_{min}}^{T_2} \frac{\partial n_{cl}}{\partial T} dT + \int_{\lambda_R}^{\lambda_2} \frac{\partial n_{cl}}{\partial \lambda} d\lambda \quad (13)$$

$$= n_{co}(T_{min}, \lambda_R) + \int_{T_{min}}^{T_2} \frac{\partial n_{cl}}{\partial T} dt + \int_{\lambda_R}^{\lambda_2} \frac{\partial n_{cl}}{\partial \lambda} d\lambda$$

If, in addition, the RI of the core has been previously evaluated at the wavelength $\lambda_R$, but at some other temperature, $T_R$, then equation (13) can be generalized further by equation (14).

$$n_{cl}(T_2, \lambda_2) = \quad (14)$$

$$n_{co}(T_R, \lambda_R) + \int_{T_R}^{T_{min}} \frac{\partial n_{co}}{\partial T} dT + \int_{T_{min}}^{T_2} \frac{\partial n_{cl}}{\partial T} + \int_{\lambda_R}^{\lambda_2} \frac{\partial n_{cl}}{\partial \lambda} d\lambda$$

In the case of the fiber optic refractometer, the "cladding" becomes an edible oil with RI, $n_o(T,\lambda)$, then equation (14) may be finally expressed $$n_o(T_2, \lambda_2) = \quad (15)$$

$$n_{co}(T_R, \lambda_R) + \int_{T_R}^{T_{min}} \frac{\partial n_{co}}{\partial T} + \int_{T_{min}}^{T_2} \frac{\partial n_o}{\partial T} dT + \int_{\lambda_R}^{\lambda_2} \frac{\partial n_o}{\partial \lambda} d\lambda$$

Equation (15) shows that if the RI of an edible oil may be compared to the RI of an optical fiber core at some temperature and wavelength $(T_{min}, \lambda_R)$, then the oil's RI may be calculated at any other temperature and wavelength $(T_2, \lambda_2)$. To do this, the temperature and dispersion characteristics of the core and oil must be known. If $$\frac{\partial n_o}{\partial T} \neq \frac{\partial n_{co}}{\partial T} \quad (16)$$

then $Pt_{min}$ may be reached by varying the temperature of the fiber optic refractometer to some value, $T_{min}$. Temperature is a parameter more easily varied in a continuous fashion than wavelength. The condition of equation (16) is necessary in order that there be some temperature where equation (12) holds true.

The core material often used in optical fibers is synthetic fused silica, an extremely homogeneous and stable form of $SiO_2$ made by either oxidizing or hydrolyzing silicon tetrachloride gas (SiCl$_4$). Its transmittance is about 92% at wavelengths from 200 nm to 3500 nm. Whereas naturally occurring SiO$_2$ (quartz) is birefringent, synthetic fused silica exhibits a uniform RI. It also has high mechanical strength and is resistant to most chemicals. Like all other materials, the RI of synthetic fused silica, $n_s(T,\lambda)$, is affected by wavelength. The phenomenon of dispersion in transparent dielectric materials normally manifests itself as a decreasing RI with increasing wavelength interspersed with infrequent resonant (anomalous) regions. The RI dispersion, $n(\lambda)$, is described by Sellmeier's general equation (17)

$$[n(\lambda)]^2 = 1 + \sum_j \frac{A_j \lambda^2}{\lambda^2 - \lambda_{oj}^2} \quad (17)$$

where $\lambda$ is the radiation wavelength; $\lambda_{oj}$ is the wavelength of the jth resonant mode (anomalous region) and the $A_j$ are constants, characteristic of the specific optical material. The equation is derived from an atomic model in which the outer electrons are assumed to be vibrating masses constrained by Hooke's law. The electrons become excited by incident electromagnetic fields and oscillate accordingly. In doing so, they generate their own electromagnetic fields which excite electrons, propagating the incident fields through the material.

Equation (17) may be expanded and re-written in a more manageable form where the coefficients, $C_k$, are characteristic of the material.

$$[n(\lambda)]^2 = C_0 + C_1\lambda^2 + C_2\lambda^{-2} + C_3\lambda^{-4} + C_4\lambda^{-6} + C_5\lambda^{-8} \quad (18)$$

Another equation for dispersion, known as Cauchy's equation, is $$n(\lambda) = K_1 + K_2\lambda^{-2} + K_3\lambda^{-4} + \ldots \quad (19)$$

It closely approximates Sellmeier's equation and can be evaluated with fewer data points. Manufacturers of synthetic bused silica provide dispersion data on their product referenced to 20.0° C.—usually at 50 to 60 discrete wavelengths. This data can be used to perform a least squares curve fit using an 8th degree polynomial as in Sellmeier's expanded equation (17). This determines the coefficients, $C_k$, resulting in silica's specific equation for $n_s(20.0,\lambda)$.

The specific coefficients of equation (18) can be determined from dispersion curves supplied by silica manufacturers (See Malitson, I. H., "Interspecimen comparison of the refractive index of fused silica," Journal of the Optical Society of America, vol 55, no. 10, 1965, pp. 1205-1209). The coefficients are:

$C_0 = 2.1045148$  $C_3 = 1.7828566(10^{10})$ $C_1 = -9.435785(10^{-9})$  $C_4 = -5.0589822(10^{13})$ $C_2 = 8.4899191(10^3)$  $C_5 = 1.1987466(10^{17})$ at 20° C. At $\lambda = \lambda_R = 594.10$ nm, the reference wavelength used in the invention's preferred embodiment, $$n_s(T_R,\lambda_R) = n_s(20.0, 594.10),$$

is equal to 1.45824 RI.

Synthetic fused silica RI exhibits a small, albeit measurable temperature coefficient, $\alpha_{ST}$. While the coefficient is affected by wavelength, it remains constant at approximately $+0.00001$ RI units/°C. between 400 nm and 700 nm.

These characteristics of synthetic fused silica illustrate its application as a highly accurate refractive index standard. Silica's characteristics are so well known that its RI can be easily compensated to account for any effects of dispersion and temperature.

The dispersion of an edible oil, like any other optical material, is not expected to be a linear function of wavelength. This is apparent from equations (20a) and (20b), which show the partial derivatives of Sellmeier's expanded equation (18) and Cauchy's equation (19).

$$\frac{\partial n_o}{\partial \lambda} = \frac{2C_1\lambda - 2C_2\lambda^{-3} - 4C_3\lambda^{-5} - 6C_4\lambda^{-7} - 8C_5\lambda^{-9}}{2\sqrt{C_0 + C_1\lambda^2 + C_2\lambda^{-2} + C_3\lambda^{-4} + C_4\lambda^{-6} + C_5\lambda^{-8}}} \quad (20)$$

$$= \frac{C_1\lambda - C_2\lambda^{-3} - 2C_3\lambda^{-5} - 3C_4\lambda^{-7} - 4C_5\lambda^{-9}}{n} \quad (a),$$

Sellmeier $$= -K_2\lambda^{-3} - K_3\lambda^{-5} \quad (b), \text{Cauchy} \quad (20)$$

Under certain conditions, $\partial n_o/\partial \lambda$ of equations (20) may be simplified. If $\Delta\lambda < \lambda$, then $\partial n_o/\partial \lambda \approx$ constant $= \beta_{o\lambda}$. Assuming that there is some convenient reference wavelength, $\lambda_R$, then $\beta_{o\lambda}$ may be calculated for a range of nearby wavelengths, $(\lambda_R - \Delta\lambda) < \lambda < (\lambda_R + \Delta\lambda)$, by using the approximation $$\beta_{o\lambda} = \frac{n(\lambda) - n(\lambda_R)}{\lambda - \lambda_R}, \lambda \approx \lambda_R \quad (21)$$

Typical constants of Cauchy's equation (19) for partially hydrogenated soybean oils are:

$K_1 = 1.44687$ $K_2 = 4.22067(10^3)$ $K_3 = 0.76294(10^8)$

Selecting $\lambda = 589.3$ nm and $\lambda_R = 594.1$ nm in equation (21) and using RI values from equation (19), gives an average value of $\beta_{o\lambda} = -4.514(10^{-5})$ RI units/nm (See Cole, C. F., Development of a Fiber Optic Refractometer to Measure the Partial Hydrogenation of Edible Oils, dissertation, Univ. of AR, Fayetteville, 1991, pp. 54-58).

The RIs of all edible oils decrease linearly with increasing temperature. The value of this temperature coefficient, $\alpha_{oT}$, varies slightly between oils produced from various plant seeds, but remains constant for a particular oil over a very wide temperature range. (See Simpson, B. W., "Refractive index-iodine value-linoleic acid-oleic acid regressions for queensland grown sunflower oil," Australian Journal of Experimental Agriculture and Animal Husbandry, vol. 17, 1977, pp. 316-318; also, Tolman, L. M., and L. S. Munson, "Refractive indices of salad oils—correction for temperature," Journal of the Society of Chemical Industry (Great Britain), vol. 24, no. 8, 1902, pp. 754-758). This is equivalent to stating that, for an edible oil, $\partial n_o/\partial T = \alpha_{oT}$ = constant, which must be determined for that particular oil. Partially hydrogenated soybean oils have $\alpha_{oT} = -3.692(10^{-4})$ RI units/°C., average.

An optical fiber refractometer used to measure edible oil refractive indices should preferably duplicate the response of the Abbe type refractometer the instrument specified for this purpose by the American Oil Chemists' Society. The Abbe refractometer is calibrated to read $n_D$, the RI referenced to the 589.3 nm sodium D line. This instrument, accurate to ±0.0001 RI units, employs a sample holder having a circulating water jacket. For testing edible oils, the sample holder temperature must be controlled between 40° and 60° C., ±0.1°. Typically, a reference temperature of 50.0° C. is used. This RI is specified as $n_D^{50.0}$. Therefore, if the fiber optic refractometer is calibrated specifically for the purpose of measuring the RI of partially hydrogenated edible oils, equation (15) becomes $$n_D^{50.0} = n_s(20.0,\lambda_R) + (10^{-5})(T_{min} - 20.0) + \qquad (22)$$
$$\alpha_{oT}(50.0 - T_{min}) + \beta_{o\lambda}(589.3 - \lambda_R)$$

where:
- $n_{co}(T_R, \lambda_R) = n_s(20.0, \lambda_R)$, the RI of silica at some reference wavelength, $\lambda_R \approx 589.3$ nm, and measured at $T_R = 20.0°$ C.
- $\partial n_{co}/\partial T = 10^{-5}$ RI units/°C., the temperature coefficient of silica.
- $\partial n_{cl}/\partial T = \alpha_{oT}$, the temperature coefficient of the edible oil.
- $\partial n_{cl}/\partial \lambda = \beta_{o\lambda}$, the constant dispersion of the edible oil.
- $T_{min}$ (°C.) = the temperature at $Pt_{min}$.
- $T_2 = 50.0°$ C.
- $\lambda_2 = 589.3$ nm This equation simplifies to the linear algorithm $$n_D^{50.0} = D + E(T_{min}) \qquad (23)$$

where D and E are constants.

$$D = n_s(20.0, \lambda_R) - 2(10^{-4}) + \alpha_{oT}(50.0) + \beta_{o\lambda}(589.3 - \lambda_R)$$

$$E = T_{min}[(10^{-5}) - \alpha_{oT}] \qquad (24)$$

In the invention's preferred embodiment:

$\lambda_R = 594.10$ nm $n_s(20.0, \lambda_R) = 1.45824$ RI $\alpha_{oT} = -3.692(10^{-4})$ RI units/°C.

$\beta_{o\lambda} = -4.514(10^{-5})$ RI units/nm and equation (23) becomes $$n_D^{50.0} = 1.43980 + 3.792(10^{-4})T_{min} \qquad (25)$$

While equation (22) has been developed considering the optical fiber sensor to be $SiO_2$ and the liquid to be an edible oil with RI to be measured under specific conditions, its general form, as given in equation (15) is applicable for any other optical material that could be used as a suitable sensor for any other liquid whose RI is to be determined.

II. DESCRIPTION OF A PREFERRED EMBODIMENT

Figure 4:
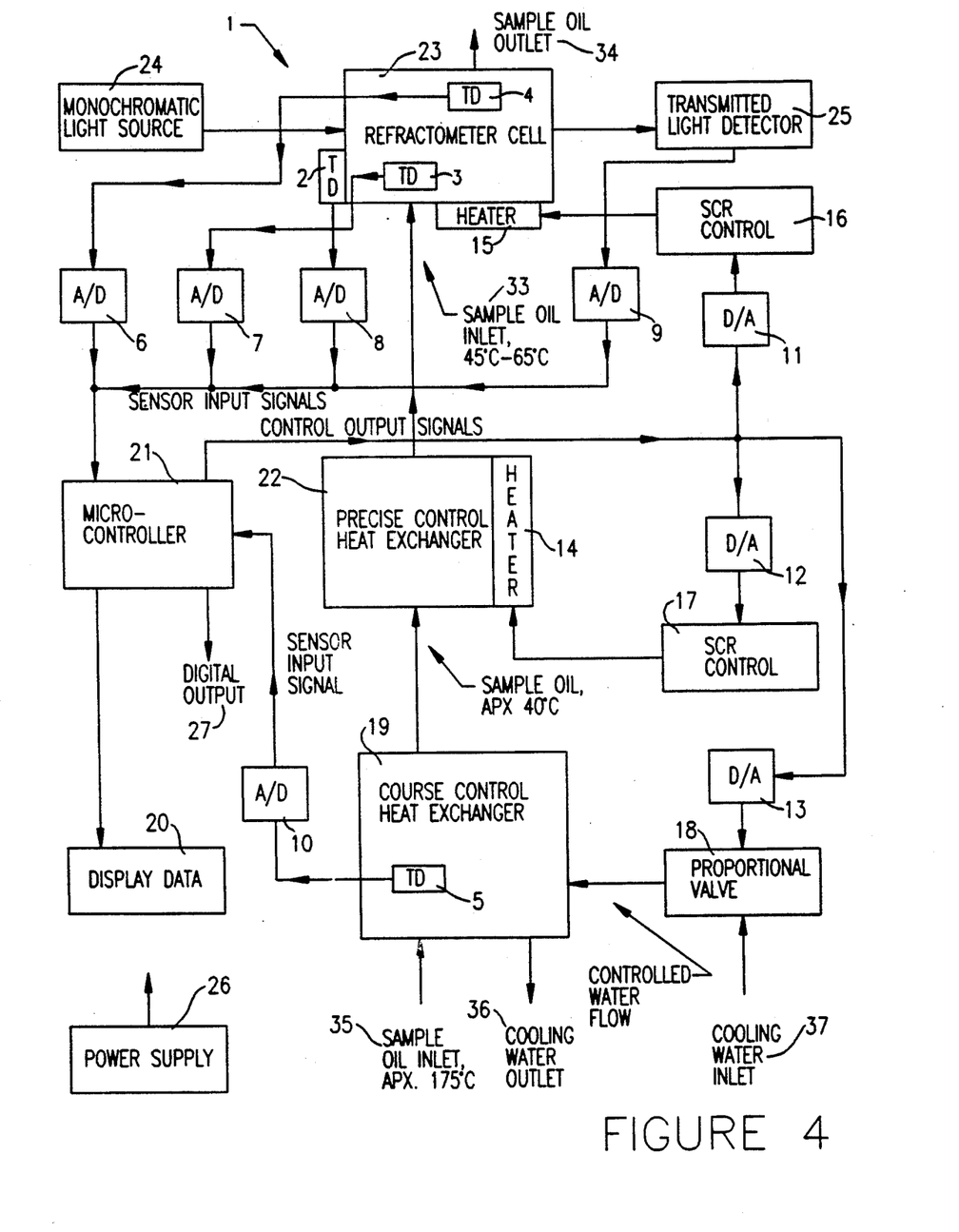
FIG. 4 is a functional block diagram of a fiber optic refractometer in accordance with the present invention.

Referring to FIG. 4, a more detailed description of the fiber optic refractometer (FOR) is given. In the preferred embodiment, the FOR system 1 receives a continuous sample flow of partially hydrogenated edible oil 35 into a course control heat exchanger 19 which cools the oil from its processing temperature of 175° C. to approximately 40° C. The control for the heat exchanger consists of a temperature detector (TD) 5, and an analog to digital (A/D) converter 10 supplying a temperature signal to a microcontroller 21. The microcontroller 21 is programmed, in part, to supply a signal to the digital to analog (D/A) converter 13 which operates a proportional flow control valve 18. Control valve 18 continuously varies the flow of cooling water 37 to the heat exchanger 19. The cooling water 37 flows through coils or grids which contact the oil within the heat exchanger 19. The microcontroller 21, in part, emulates a proportional-integral-derivative (PID) controller to maintain the oil temperature flowing out of the heat exchanger 19 at approximately 40° C. ±1° C. The cooling water leaving the heat exchanger 19 at outlet 36 may be used for other purposes or discarded.

The partially hydrogenated oil flows from the course control heat exchanger 19 into the precise control heat exchanger 22 and from there into the refractometer cell 23. Light from the monochromatic light source 24 passes into the refractometer cell 23 where the light interacts with the hydrogenated oil and passes to the transmitted light detector 25. A signal proportional to the transmitted light power, Pt, is sent from the detector 25 to A/D converter 9 thence to the microcontroller 21. The microcontroller 21 is programmed, in part, to supply a signal to D/A converter 12 which operates a silicon controlled rectifier (SCR) control 17. SCR Control 17 supplies continuously varying electrical power to heater 14 mounted in thermal contact with heat exchanger 22. The microcontroller 21, in part, emulates a PID controller to maintain the light power received by the transmitted light detector 25 at a minimum, $Pt_{min}$.

Temperature detectors (TD) 3 and 4 sense the oil temperature within the refractometer cell 23. They are connected to A/D converters 6 and 7, respectively, which supply temperature signals to microcontroller 21. The microcontroller 21 is programmed, in part, to calculate the average temperature, $T_{avg}$, of TDs 3 and 4. Referring to FIG. 3, if the liquid within the refractometer cell 23 has a negative refractive index (RI) temperature coefficient, the microcontroller 21, in part, will be programmed to perform the following general control: (1) If $T_{avg}$ is decreasing and Pt is increasing, or if $T_{avg}$ is increasing and Pt is decreasing, SCR controller 17 shall supply more power to heater 14; (2) if $T_{avg}$ is increasing and Pt is increasing, or if $T_{avg}$ is decreasing and Pt is decreasing, SCR controller 17 shall supply less power to heater 14. During normal operation in the preferred embodiment, the temperature range of the sample oil at inlet 33 of the refractometer cell 23 should be from 45° C. to 65° C.

The PID controller emulation for the precise control heat exchanger 22 shall operate slightly under-damped so that the oil temperature within the refractometer cell 23 shall oscillate about $T_{min}$ by approximately ±0.1° C. It is not necessary to maintain $T_{avg}$ at $T_{min}$; $T_{avg}$ must simply be sampled in a sufficient manner to assure accurate recording of values concurrent with $Pt_{min}$. The actual value of $Pt_{min}$ is not important.

The microcontroller 21, in part, samples the oil temperature, $T_{min}$, at $Pt_{min}$ and calculates the refractive index of the hydrogenated oil using the linear algorithm of equation (23).

The sample flow of hydrogenated oil leaving the refractometer cell 23 at outlet 34 may either be returned to the hydrogenated process or discarded.

The microcontroller 21 may, in part, supply information to a display 20 that can show values of refractive index or other information pertinent to the hydrogenation process. The microcontroller 21 may also, in part, supply a digital output 27 to external devices such as process controllers that operate the hydrogenation process itself. In doing so, the FOR system 1 could become part of an overall system for controlling the complete hydrogenation process.

In order to compensate for heat loss and thermal gradients within the refractometer cell 23, the microcontroller 21 shall, in part, receive a temperature signal, $T_{cell}$, through A/D converter 8, sent from TD 2 mounted on the surface of the refractometer cell 23. The microcontroller 21 shall compare $T_{cell}$ with $T_{avg}$ and provide a control signal to D/A converter 11 thence to SCR control 16 which supplies continuously varying power to heater 15 mounted on the surface of the refractometer cell 23. The microcontroller 21, in part, emulates a PID controller to maintain the refractometer cell 23 at the same temperature as the hydrogenated oil flowing through it. The result is reduced thermal gradients through the oil within the cell.

In this embodiment, the monochromatic light source 24 is a #LSTP-00100 tunable laser manufactured by PMS Electro-optics, Inc., Boulder, Colo., tuned to a wavelength, $\lambda_R = 594.10$ nm. The transmitted light detector 25 is a #550-2 silicon cell photo-detector and #550-1 photometer manufactured by EG&G Electro-optics, Salem, Mass.

Power supply 26 provides all the necessary power for the electrical and electronic elements that comprise the FOR system 1.

Figure 5:
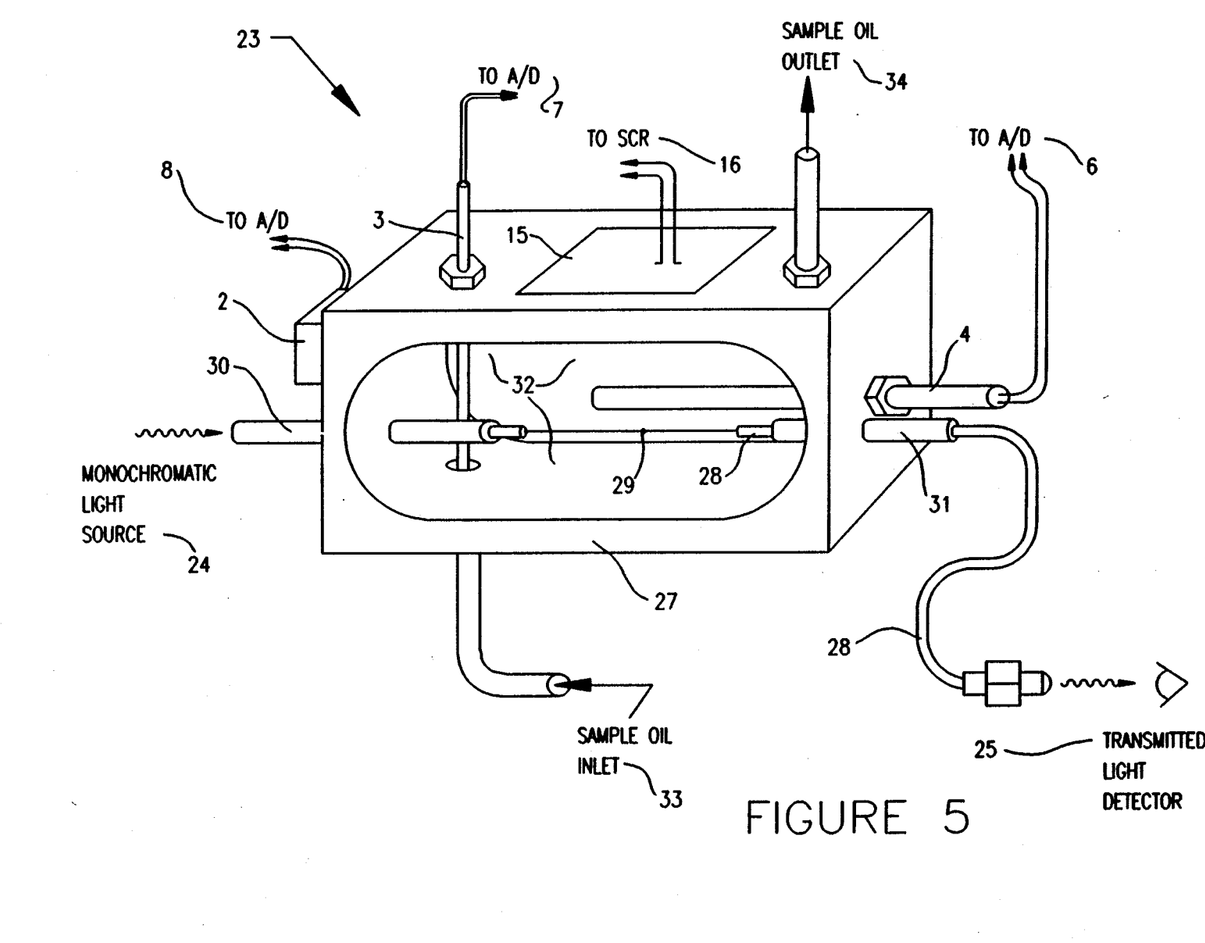
FIG. 5 shows a fiber optic refractometer cell in detail.

FIG. 5 shows a more detailed view of an embodiment of the refractometer cell 23. A plate covering the front of the cell has been removed to show the cell interior. The cell housing 27 is machined from solid aluminum for good thermal conductivity. The sample of partially hydrogenated oil enters the cell cavity 32 through inlet 33 and flows out of the cell through outlet 34. Optical fiber 28 passes through the cell cavity 32. A section 29 of the optical fiber has the jacket and cladding removed, exposing the core to the oil. The optical fiber 28 is held in place by stainless steel sleeves 30 and 31. The fiber is cemented into the sleeves and the sleeves are, in turn, cemented to the cell housing 27. In this embodiment, the optical fiber 28 is #SPC100N Superguide PCS manufactured by Fiberguide Industries, Stirling, N.J. The fiber has a nylon jacket and a plastic cladding extruded over a 100 um diameter synthetic fused silica core. The jacket and cladding were removed by immersing the fiber section in 18 molar sulfuric acid. Temperature detector 3 is mounted to sense the oil temperature as it enters the cell cavity 32; temperature detector 4 is mounted to sense the oil temperature as the oil flows along the exposed section 29 of the optical fiber 28. In this embodiment, the oil temperature detectors 3 and 4 are 100Ω platinum resistance devices, 0.00385Ω/Ω/°C., style 4150, manufactured by YSI, Inc., Yellow Spring, Ohio. The detectors are calibrated over the temperature range 25° C.–70° C. The refractometer cell temperature detector 2 is a type J thermocouple, #SA1-J, manufactured by Omega Engineering, Inc., Stamford, Conn.

The refractometer cell heater 15 is a 10 watt, 120 volt, flexible etched foil unit, #010020C1-PFAS, manufactured by Watlow Mfg., St. Louis, Mo.

The A/D converters 6, 7, 8, 9 and 10, as well as the D/A converters 11, 12 and 13, are the 6B Series of signal conditioners manufactured by Analog Devices, Norwood, Mass.

Although the invention has been described in conjunction with the foregoing specific embodiment, many alternatives, variations, and modifications will be apparent to those of ordinary skill in the art. Those alternatives, variations, and modifications are intended to fall within the scope of the following appended claims.

I claim:

1. A method for measuring the refractive index of a fluid, comprising the steps of:
   a) radiating light at a known wavelength $\lambda_R$ into an optical waveguide having a refractive index $n_{co}$ and measuring the optical power transmitted therethrough, wherein the value of $n_{co}$ is known at wavelength $\lambda_R$ as a function of temperature, and further wherein at least part of the wave guide is in contact with a fluid whose refractive index is to be measured;
   b) varying the temperature of the fluid and fluid contacted waveguide section until the transmitted optical power through the waveguide reaches a minimum, at which point the refractive indices of the waveguide and fluid are deemed to be equal;
   c) measuring the temperature $T_{min}$ at which the transmitted optical power minimum occurs; and,
   d) determining the refractive index of the fluid at wavelength $\lambda_R$ and temperature $T_{min}$ from the known value of $n_{co}$ at $T_{min}$.

2. The method as set forth in claim 1 wherein the fluid whose refractive index is to be measured is a member of a known class of fluids with each member of the class uniquely having a refractive index known as a function of temperature and additionally comprising the step of identifying the specific class member represented by the fluid whose refractive index is measured.

3. The method as set forth in claim 2 wherein the class is a specific oil having as members oils with differing hydrogenation states, the refractive index $n_o$ of the oil is known as a function of hydrogenation state and temperature, and further comprising the step of ascertaining the hydrogenation state of the oil from the measured refractive index.

4. The method as set forth in claim 3 wherein:
   the refractive index of the waveguide, $n_{co}$, is known at a first reference temperature, $T_R$, and a first reference wavelength, $\lambda_R$;
   the dependence of $n_{co}$ on temperature, $\partial n_{co}/\partial T$ is known;
   the refractive index, $n_o$, of the specific oil, being at one of a plurality of hydrogenation states, is measured at $T_{min}$, the temperature at which the transmitted optical power through the waveguide reaches a minimum;
   the dependence of $n_o$ on temperature, $\partial n_o/\partial T$, and the dependence of $n_o$ on wavelength, $\partial n_o/\partial \lambda$, are known; and
   the refractive index of the oil being measured, referenced to a second temperature, $T_2$, and a second wavelength, $\lambda_2$, is calculated by the formula:

$$n_o(T_2, \lambda_2) = n_{co}(T_R, \lambda_R) +$$

-continued $$\int_{T_R}^{T_{min}} \frac{\partial n_{co}}{\partial T} dT + \int_{T_{min}}^{T_2} \frac{\partial n_{co}}{\partial T} dT + \int_{\lambda_R}^{\lambda_2} \frac{\partial n_o}{\partial \lambda} d\lambda$$

where $n_o(T_2,\lambda_2)$ corresponds to a specific hydrogenation state of the oil.

5. The method as set forth in claim 1 wherein the light radiated into the waveguide is monochromatic light at wavelength $\lambda_R$.

6. The method as set forth in claim 1 wherein the optical waveguide is a multimodal step index optical fiber comprising a core with refractive $n_{co}$ surrounded by a cladding, and further wherein the section of the waveguide in contact with the fluid is a section of the fiber with its cladding removed.

7. A refractometer for measuring the refractive index of a fluid, comprising:
   an optical waveguide with a refractive index whose value is known as a function of temperature;
   a cell for containing a sample of a fluid with a section of the waveguide in contact with the fluid within the cell;
   means for radiating light into the waveguide and means for sensing the optical power transmitted therethrough;
   means for sensing and regulating the temperature of the fluid within the cell; and
   means for automatically varying the temperature of the fluid within the cell in accordance with the sensed optical power until the optical power transmitted through the waveguide reaches a minimum at a temperature $T_{min}$ at which point the refractive index of the fluid and the refractive index of the waveguide are deemed to be equal.

8. The refractometer as set forth in claim 7 further comprising means for calculating the refractive index of the fluid at temperature $T_{min}$ from the known refractive index of the waveguide whose value is known as a function of temperature.

9. The refractometer as set forth in claim 7 further comprising means for calculating the refractive index of the fluid at a specified temperature from a known temperature dependence of the fluid's refractive index.

10. The refractometer as set forth in claim 9 further comprising means for calculating the refractive index of the fluid at a specified wavelength from a known wavelength dependence of the fluid's refractive index.

11. The refractometer as set forth in claim 7 wherein the light radiated into the waveguide is monochromatic light at a known wavelength $\lambda_R$.

12. The refractometer as set forth in claim 7 wherein the optical waveguide is a multimodal step index optical fiber comprising a core with refractive index $n_{co}$ surrounded by a cladding, and further wherein the section of the waveguide in contact with the fluid is a section of the fiber with its cladding removed.

13. The refractometer as set forth in claim 7 further comprising means for regulating the temperature of the cell so as to reduce thermal gradients through the fluid within the cell.

14. An apparatus for measuring the hydrogenation state of an oil where the value of the oil's refractive index as a function of its hydrogenation state and temperature is known, comprising:
   an optical waveguide with a refractive index whose value at wavelength $\lambda_R$ is known as a function of temperature;
   a cell for containing a sample of an oil with a section of the waveguide in contact with the oil within the cell;
   means for radiating light of wavelength $\lambda_R$ into the waveguide and means for sensing the optical power transmitted therethrough;
   means for sensing and regulating the temperature of the oil within the cell;
   means for automatically varying the temperature of the oil within the cell in accordance with the sensed optical power until the optical power transmitted through the fiber reaches a minimum at a temperature $T_{min}$ at which point the refractive index of the oil and the refractive index of the waveguide are deemed to be equal;
   means for calculating the refractive index of the oil at temperature $T_2$ from the known waveguide refractive index at $T_{min}$ whose value is known as a function of temperature; and
   means for calculating the hydrogenation state of the oil from the calculated refractive index of the oil at $T_2$ and the known dependence of the oil's refractive index on hydrogenation state and temperature.

15. The apparatus as set forth in claim 14 wherein the dependence of the oil's refractive index on hydrogenation state and temperature is known for a wavelength $\lambda_2$ and further comprising means for calculating the refractive index of the oil at wavelength $\lambda_2$ from a known dispersion relationship for the oil.

16. The apparatus as set forth in claim 14 wherein the light radiated into the waveguide is monochromatic light at wavelength $\lambda_R$.

17. The apparatus as set forth in claim 14 wherein the optical waveguide is a multimodal step index optical fiber comprising a core with refractive index $n_{co}$ surrounded by a cladding, and further wherein the section of the waveguide in contact with the fluid is a section of the fiber with its cladding removed.

18. The apparatus as set forth in claim 14 further comprising means for regulating the temperature of the cell so as to reduce thermal gradients through the oil within the cell.

* * * * *